United States Patent [19]
Piso

[11] 4,208,625
[45] Jun. 17, 1980

[54] CAPACITIVE MEASURING SYSTEM WITH AUTOMATIC CALIBRATION

[75] Inventor: John S. Piso, Framingham, Mass.
[73] Assignee: Micro Sensors, Inc., Holliston, Mass.
[21] Appl. No.: 898,120
[22] Filed: Apr. 20, 1978

Related U.S. Application Data

[63] Continuation-in-part of Ser. No. 823,107, Aug. 9, 1977, abandoned, which is a continuation of Ser. No. 660,398, Feb. 23, 1976, abandoned.

[51] Int. Cl.² .................................................. G01R 27/26
[52] U.S. Cl. .................................... 324/61 R; 324/130
[58] Field of Search ........................... 324/61 R, 130

[56] References Cited
U.S. PATENT DOCUMENTS

| | | | |
|---|---|---|---|
| 3,761,810 | 9/1973 | Fathauer | 324/61 R |
| 3,879,660 | 4/1975 | Piso | 324/61 R |
| 3,971,272 | 7/1976 | Felix et al. | 324/61 R X |
| 4,016,790 | 4/1977 | Felix et al. | 61 R X/ |
| 4,060,965 | 12/1977 | Schwartz | 324/61 R X |

Primary Examiner—Gerard R. Strecker
Attorney, Agent, or Firm—Parmelee, Johnson, Bollinger & Bramblett

[57] ABSTRACT

In a device for continuously monitoring the characteristics of a moving filament, such as the denier of an extended synthetic yarn, by passing the filament through a capacitive sensor to develop an electrical signal representing an absolute measurement of the filament with reference to a prescribed datum, the problem of measurement signal drift arising from contamination of the capacitive sensor is obviated by developing compensating signals to be combined with the filament measurement signal. The compensating signals are digitally formed and stored, thereby eliminating drift in the compensating signals themselves. The compensating signals are developed in an auto-calibration circuit, including an auto-zero circuit and an auto-gain circuit, which receives the measurement signal from the capacitive sensor. While the sensor is vacant, the auto-zero circuit digitally counts clock pulses to generate a digital output, converts the digital output into an analog signal varying with the digital count, detects a prescribed comparison between the analog signal and the input measurement signal, and stops the clock pulse count at a zero compensating value when the comparison is detected. Then, the auto-gain circuit applies an unbalanced drive to the sensor, digitally counts clock pulses to generate a digital output, and varies the measurement signal gain with the digital output. The circuit detects a prescribed comparison between the gain-adjusted measurement signal and a standardized output signal, and stops the clock pulse count at a gain compensating value when the prescribed comparison is detected.

31 Claims, 8 Drawing Figures

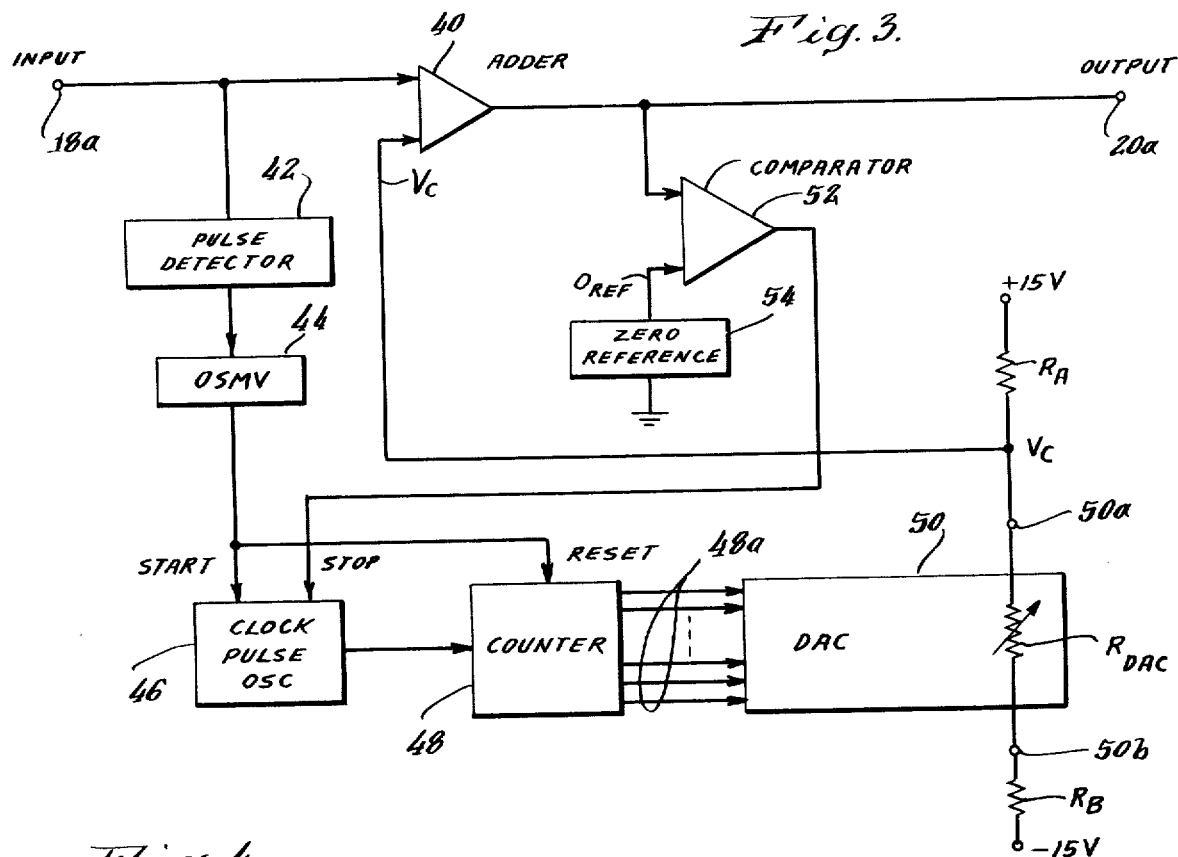
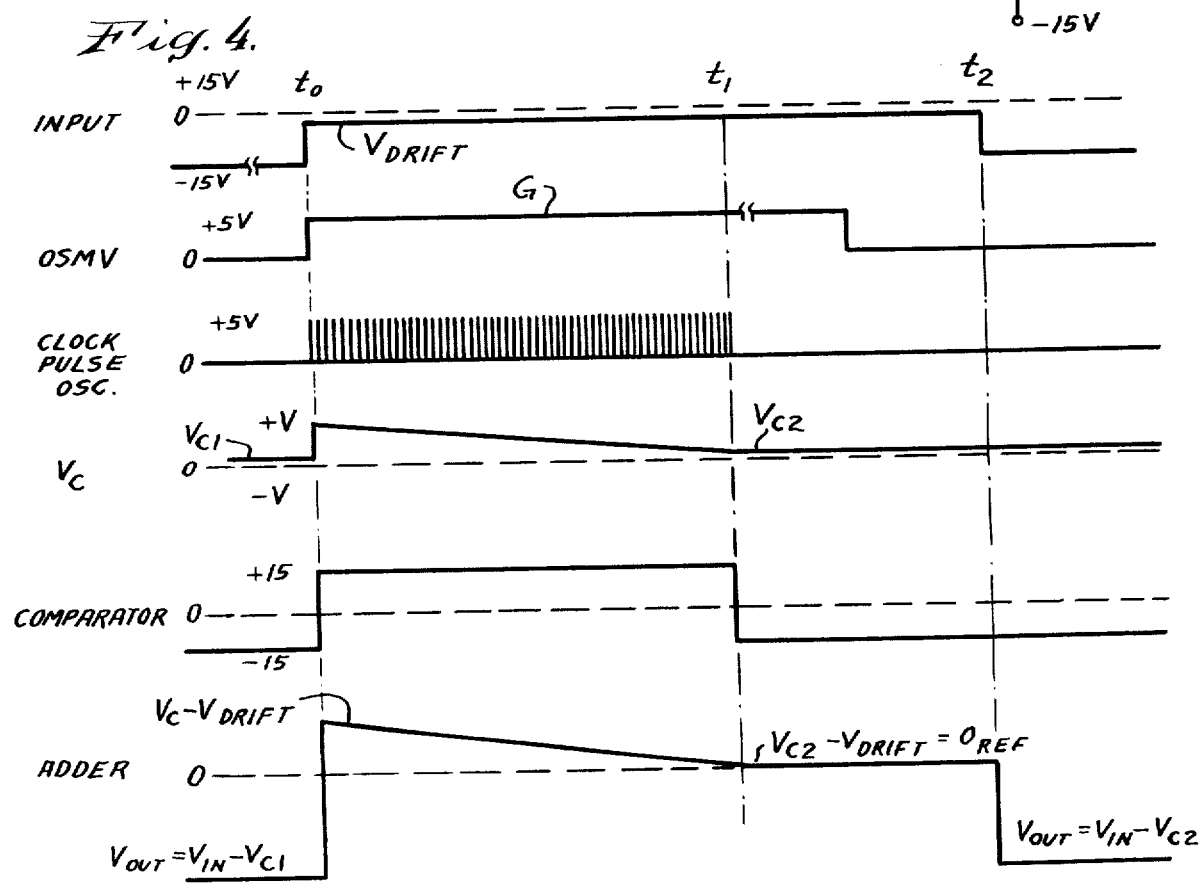

CAPACITIVE MEASURING SYSTEM WITH AUTOMATIC CALIBRATION

This is a continuation-in-part of application Ser. No. 823,107, filed Aug. 9, 1977, and now abandoned, which was a continuation of application Ser. No. 660,398, filed Feb. 23, 1976, and now abandoned.

BACKGROUND OF THE INVENTION

1. Field of the Invention

This invention relates to systems and methods for continuously measuring and monitoring the characteristics of a moving filament, such as the denier of a synthetic yarn, by passing the filament through a capacitive sensor to develop an electrical signal representing an absolute measurement of the filament, with reference to a prescribed datum or zero point. For example, denier is a unit of fineness for yarn equivalent to 1 gram per 9,000 meters of length, referred to zero. Thus a 15-denier weighs 15 grams per 9,000 meters. More particularly, this invention relates to a means and method for abrogating errors arising from slowly occurring variations in the capacitive sensor.

2. Description of the Prior Art

Devices and methods for capacitively monitoring the characteristics of a continuously moving filament are known. In one advantageous device, disclosed in U.S. Pat. No. 3,879,660 to Piso, a filament is passed through a capacitive sensor to develop an absolute measurement of the filament with reference to a prescribed datum or zero point, thus permitting the monitoring of characteristics such as the denier of synthetic yarn filaments, with the absolute measurement of denier being made available for utilization, e.g., to give an alarm if the denier measurement is outside a prescribed range of acceptable deniers.

An example of the use of such a filament monitoring device is shown schematically in FIG. 1, wherein a filament F is extruded from an extruding head E and is to be wound upon a bobbin B. The filament F passes through a slot S in a capacitive sensor head H, which is arranged to supply, on output line L, an electrical signal which varies with the capacitance of filament F, and thereby provides a measurement of the filament's denier. It has been learned that as filaments are monitored in sensor heads H, contaminants from various sources build up between the capacitor plates in sensing head H, causing the signal on line L to drift and no longer provide an accurate absolute measurement of the capacitance of filament F.

Heretofore errors due to the buildup of contaminants in sensor heads H has been counteracted by periodic cleaning of the sensor heads. However, relatively common-place filaments F promote a rapid contaminant buildup and necessitate frequent cleaning. For example, low denier filaments may contain agents which contaminate the sensor head and require it to be examined and cleaned as much as twice a week. High denier filaments, such as those used for tire cords, are subject to flaking, and sometimes have an oil finish, which lead to rapid contaminant buildup and require more frequent cleaning.

Cleaning of sensor heads necessarily requires substantial interruption of monitoring, and prevents full utilization of capacitive measurement systems in filament monitoring if accurate absolute measurements are to be maintained.

SUMMARY

It is a principal object of the present invention to provide an improved capacitive measurement and monitoring system able to efficiently maintain accurate absolute measurements. Specific objects of the invention are to provide a capacitive measurement and monitoring system in which drift arising from variations in the capacitive sensor can be easily and automatically counteracted, in which cleaning of sensor heads is postponed or eliminated entirely, and in which no new measurement inaccuracies are introduced. It is a further object of the invention to provide a capacitive measurement and monitoring system more suitable for commercial use.

In preferred embodiments of the invention, to be described hereinbelow in detail, a moving filament is continuously monitored by passing the filament through a capacitive sensor to develop an electrical signal to represent an absolute measurement of the filament with reference to a prescribed datum or zero point. Means are provided for developing zero and gain compensating signals which are to be combined with the filament measurement signal to compensate for measurement signal drift arising from variations in the capacitive sensor.

The zero compensating signal is developed by digitally forming and storing a signal to be converted into the compensating signal, thereby minimizing errors arising from drift in the zero compensating signal itself. The means developing the zero compensating signal is arranged to produce a clock train, to digitally count the clock pulses and to generate an analog output signal varying with the digital count, to detect a prescribed comparison between the analog signal and the input measurement signal absent the filament, and to stop the clock pulse count when the prescribed comparison is detected. The digital count and associated analog output signal thus become fixed at a level related to the amount of accumulated signal drift in the capacitive sensor.

The gain compensating signal is also digitally formed and stored, thereby minimizing errors arising from drift in the gain compensating signal itself. The circuit for developing the gain compensating signal is arranged to apply an unbalanced drive to the bridge, to produce a clock pulse train, to digitally count the clock pulses and to adjust the gain of the measurement signal. The circuit detects a predetermined comparison between the gain-adjusted measurement signal and a standardized signal, and stops the clock pulse count when the comparison is detected. The digital count thus becomes fixed at a level related to the amount of accumulated drift in gain of the capacitive sensor and, along with the zero compensating signal, provides subsequent accurate absolute measurements.

In a further aspect of the invention, the means developing the compensating signals continuously receives the filament measurement signal and has means for detecting variations in the measurement signal corresponding to removal of the filament from the capacitive sensor, so that each time the filament is removed a new compensating signal will be developed automatically. The foregoing arrangement thus permits signal drifts arising from contaminants in the sensor head to be compensated very rapidly, automatically, and without requiring the sensor head to be removed from service for a significant time or to be cleaned except at considerably extended intervals, if at all.

Other objects, aspects and advantages of the invention will be pointed out in, or apparent from, the detailed description hereinbelow, considered together with the following drawings.

DESCRIPTION OF THE DRAWINGS

FIG. 3 is a schematic diagram of a circuit for developing a zero compensating signal to compensate for measurement signal drift in accordance with the present invention;

FIG. 4 is a graph of wave forms at selected points in the circuit of FIG. 3;

DESCRIPTION OF THE PREFERRED EMBODIMENT

Figure 1:
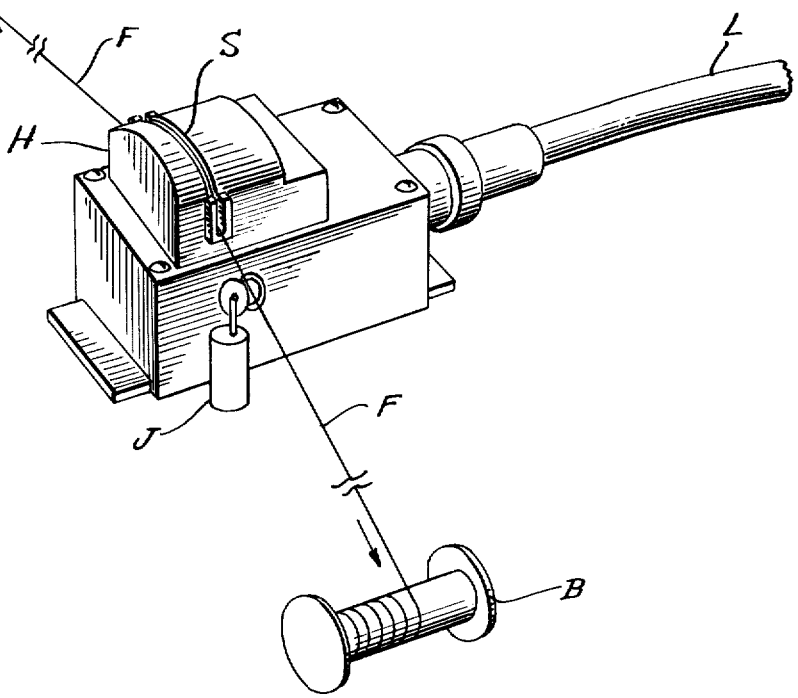
FIG. 1 is a schematic perspective view showing portions of a capacitive filament monitoring system in operation.
Figure 2:
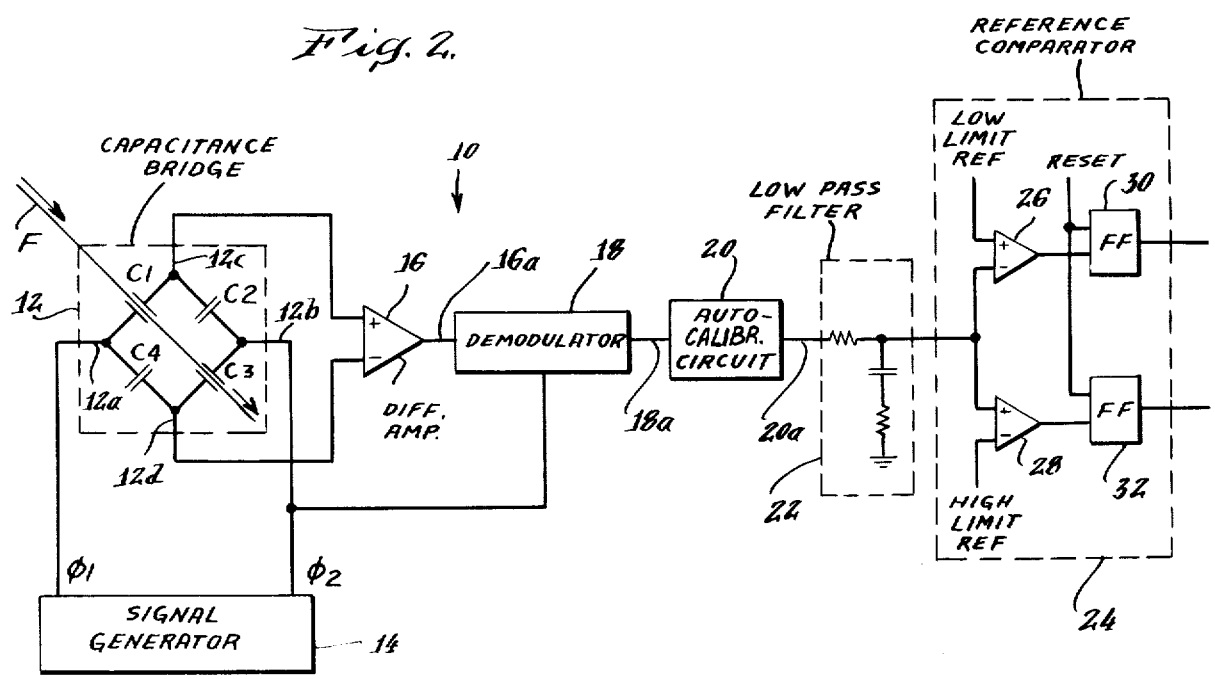
FIG. 2 is a schematic view of a capacitive filament monitoring system in accordance with the present invention.

A capacitive measurement and monitoring system 10 arranged in accordance with the present invention to compensate for measurement signal drift arising from variations in the capacitive sensor is shown in FIG. 2. As diagrammatically illustrated, system 10 utilizes a sensor head forming a capacitance bridge 12 which is driven by a signal generator 14 to provide signals first to a differential amplifier 16 and then to a demodulator 18 in the manner described in U.S. Pat. No. 3,879,660. Briefly, in such an arrangement the filament F passes between opposed capacitors C1 and C3 of the capacitance bridge 12. Signal generator 14 applies sinosoidal signals $\phi 1$ and $\phi 2$, which are 180° out of phase, to bridge input terminals 12a and 12b. At bridge output terminals 12c and 12d there appear signals 180° out of phase with amplitudes proportional to the difference between the capacitance associated with capacitors C1 and C3 and the capacitance associated with capacitors C2 and C4. The signals at terminals 12c and 12d are applied to the plus and minus inputs of the differential amplifier 16, to produce an output with an amplitude proportional to the difference in the capacitance associated with the two sets of capacitors C1, C3 and C2, C4 (i.e., a signal modulated by the capacitive characteristics of filament F). The output from differential amplifier 16 is applied to demodulator 18 together with signal $\phi 2$ from generator 14, to yield a demodulated dc signal at terminal 18a which is proportional to the difference in capacitance associated with the capacitor pairs C1, C3 and C2, C4. Since capacitors C1 through C4 are physically identical, the signal at terminal 18a is an absolute measurement of a capacitance of filament F. However, as contaminants build up in capacitors C1 through C4, the filament measurement signal at the demodulator output 18a will drift and no longer accurately represent the characteristic, such as denier, of filament F that is to be monitored.

In accordance with the present invention, the filament measurement signal from demodulator 18 is applied to an auto-calibration circuit 20 which, as described below, develops at least one compensating signal which is combined with the filament measurement signal to compensate for the measurement signal drift which arises from contaminant accumulation in the capacitive sensor. The compensated filament measurement signal at the output terminal 20a of auto-calibration circuit 20, which is an accurate absolute measurement, then may be applied through a low pass filter 22 to a utilization circuit 24 such as the illustrated reference comparator, which is arranged with comparators 26, 28 and flip-slops 30, 32 to generate outputs whenever the compensated filament measurement signal goes below a predetermined low limit, or above a predetermined high limit applied respectively to comparators 26, 28. Other typical utilization circuits include meters, strip charts, recorders or process control devices.

Figure 5:
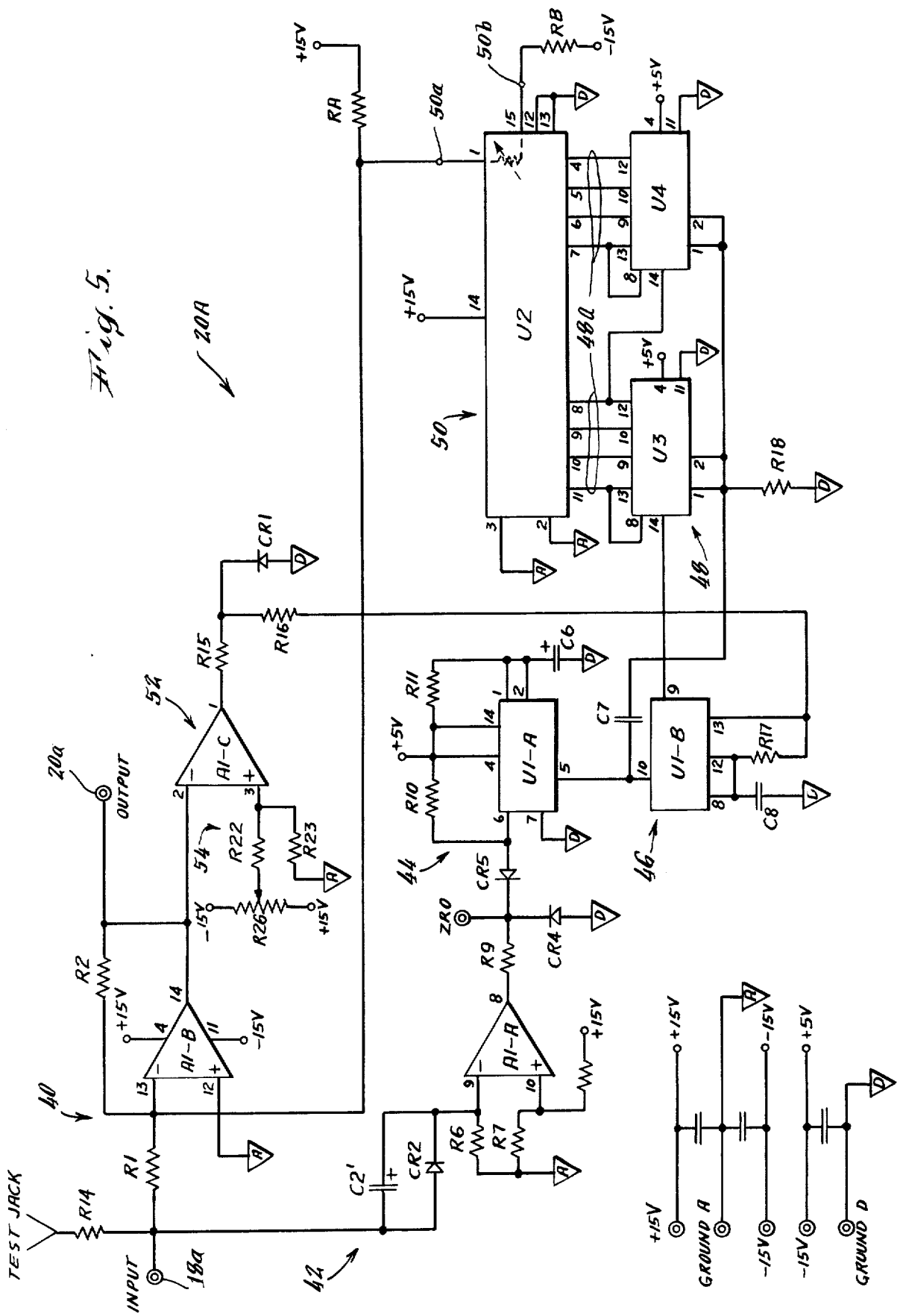
FIG. 5 is a schematic diagram illustrating details of the embodiment of FIG. 3.

The auto-calibration circuit 20 of FIG. 2 for providing auto-zero compensation is illustrated in greater detail in FIGS. 3 through 5. The circuit receives an input signal at terminal 18a from demodulator 18, which signal is a dc measurement signal varying with sensed capacitance and subject to drift arising from contamination of the capacitive elements. The input filament measurement signal is combined in an adder 40 with a compensating signal $V_c$, developed as described below, to yield a measurement signal at output terminal 20a providing an absolute measurement of the filament which is accurately referred to a prescribed datum notwithstanding variations in the capacitive sensor.

The auto-zero circuit 20 is arranged to develop a new compensating signal $V_c$ whenever filament F is lifted out of slot S in sensor head H, either manually or mechanically as with a solenoid J. As will be evident from the following explanation, the compensating signal is developed rapidly as thus it is unnecessary for the filament extruding process to be interrupted in order for compensation to take place.

The input measurement signal at terminal 18a is applied to a pulse detector 42 which detects the large scale variation in the measurement signal at terminal 18a which corresponds to removal of the filament from the capacitive sensor. The recognition of the existence of such a pulse triggers a one-shot multivibrator 44 to generate an output gate pulse which simultaneously turns on a clock pulse oscillator 46 and resets a digital counter 48. The output of the clock pulse oscillator, which is a train of clock pulses beginning at the leading edge of the gate pulse from multivibrator 44, drives digital counter 48 to generate, on output lines 48a, a digital zero-compensating output signal representing the accumulated increasing count of the clock pulses. The digital count on output lines 48a is supplied to a digital-to-analog converter 50 which is arranged to provide an analog output at terminals 50a, 50b which varies with the digital count in counter 48. The output of the illustrated digital-to-analog converter 50 is a resistance $R_{DAC}$ whose value decreases as the clock pulse train continues. The decreasing resistance $R_{DAC}$ is placed in series with resistors $R_A$ and $R_B$ connected respectively to positive and negative voltages of, e.g., +15 volts and −15 volts. These resistances and voltage sources form a voltage divider which develops, at terminal 50a, the compensating signal Vc which is applied as one input to adder 40. As resistance $R_{DAC}$ decreases, the compensating signal Vc, which is an analog signal, also decreases.

The measurement signal at input 18a, developed in sensor head H absent the filament F, is combined with the decreasing compensating signal Vc in adder 40. The decreasing adder output is applied to one input of comparator 52. The other input of comparator 52 is connected to a zero reference circuit 54 which defines the datum or zero point to which the output signal at terminals 20a is to be referred. When the output of the adder 40 matches the datum signal defined by zero reference circuit 54, the comparator 52 generates an output to stop the clock pulse oscillator 46 from generating any further clock pulses. The counter 48 maintains its digital count, and the digital-to-analog converter maintains its output resistance $R_{DAC}$, so that the appropriate zero compensating signal $V_c$ continues to be applied to adder 40. When the filament F is reintroduced in the slot S in capacitive sensor head H, the filament measurement signal at input 18a will be offset by the fixed compensation signal $V_c$ corresponding to the amount of accumulated signal drift arising from contaminants in the capacitive sensor. The output at terminal 20a then will be a measurement signal which is appropriately zeroed.

The operation of auto-zero circuit 20 is shown graphically in FIG. 4. As illustrated in FIG. 4, a compensating signal $V_{c1}$ exists prior to time $t_0$, filament F is removed from sensor head H. The measurement voltage applied to input terminal 18a then measures accumulated drift and has a value $V_{drift}$. As the filament is removed at time $t_0$, multivibrator 44 generates a gate pulse G whose leading edge causes clock pulse oscillator 46 to begin generating pulses, and causes counter 48 to begin counting the pulses from a reset condition. The compensating signal $V_c$ jumps to a value $+V$ and begins steadily to decrease. The output of the adder is $V_c - V_{drift}$, which decreases until time $t_1$ when the compensating signal reaches a value $V_{c2}$ which, when combined with $V_{drift}$, matches the zero reference signal from circuit 54 and comparator 52 stops clock pulse oscillator 46. The compensating signal thereafter stays fixed to value $V_{c2}$ and, at a time $t_2$ when the filament is returned to sensor head H, the output voltage at terminal 20a is the input measurement signal (containing drift) minus $V_{c2}$, which is an appropriately zeroed measurement signal.

The auto-zero circuit 20, as described above, provides a compensating signal $V_c$ which can be generated quickly, for example within a fraction of a second. The compensating signal itself relatively free from drift effects since its value is digitally stored in counter 48, and is converted in a digital-to-analog converter, a device relatively free from drift. The pulse detector 42 permits automatic operation to be initiated simply by lifting the filament from sensor head H. Alternatively, if the filament is to be removed from slot S with a solenoid or like device, a separate starting signal can be provided, using gate pulse G to time the duration of filament absence from slot S. It should be noted further that auto-zero circuit 20 effects a comparison of the prescribed datum with the output of the adder circuit which combines the filament measurement signal with the compensating signal $V_c$, and thereby automatically compensates for any drift which may arise in adder 40.

FIG. 5 illustrates in detail the construction of an auto-zero circuit 20A of the type described above. Pulse detector 42 has an input high pass filter formed with capacitor C2 and diode CR2 at the input to amplifier A1-A which responds to gross changes in the input signal to trigger multivibrator 44. As shown, a terminal ZRO at the input to multivibrator 44 is provided to manually apply a trigger signal. The multivibrator 44 is formed with an oscillator section U1-A arranged to function in a monostable mode, and to have a gate pulse output to start clock pulse oscillator 46. Clock pulse oscillator 46 is formed with an oscillator section U1-B connected for free running operation at, e.g., 1 K Hertz. The counter 48 is formed with two four bit counters U3 and U4, and has eight output lines 48a connected to digital-to-analog converter 50. The output voltage at pin 1 of converter 50, which corresponds to terminal 50a in the converter shown in FIG. 3, is fed to the input of adder 40, which is formed with an operational amplifier A1-B. Comparator 52 is formed with an amplifier section A1-C, with a zero reference circuit 54 connected to its positive input terminal. The zero reference circuit 54 comprises a potentiometer R26 connected between positive and negative voltage sources of +15 volts and −15 volts with the intermediate potentiometer contact connected through a resistor R22 to the positive terminal of comparator 52. Accordingly, the zero reference can be adjusted or trimmed to provide accurate calibration.

In FIG. 5, the numbers adjacent the various amplifiers, oscillators, counters and converter represent the pin numbers of exemplary devices as applied by the manufacturers thereof. As illustrated, the amplifier sections A1-A through A1-C are sections of a National Semiconductor model 324 component, the oscillator sections U1-A and U1-B are National Semiconductor model 556 components, the counter sections U3 and U4 are Texas Instruments model 74L93 components, and the digital-to-analog converter U2 is an Analog Devices, Inc. model AD 7520KN component. The ground connections indicated as A and D are developed as shown in the lower lefthand corner of FIG. 5.

Figure 6:
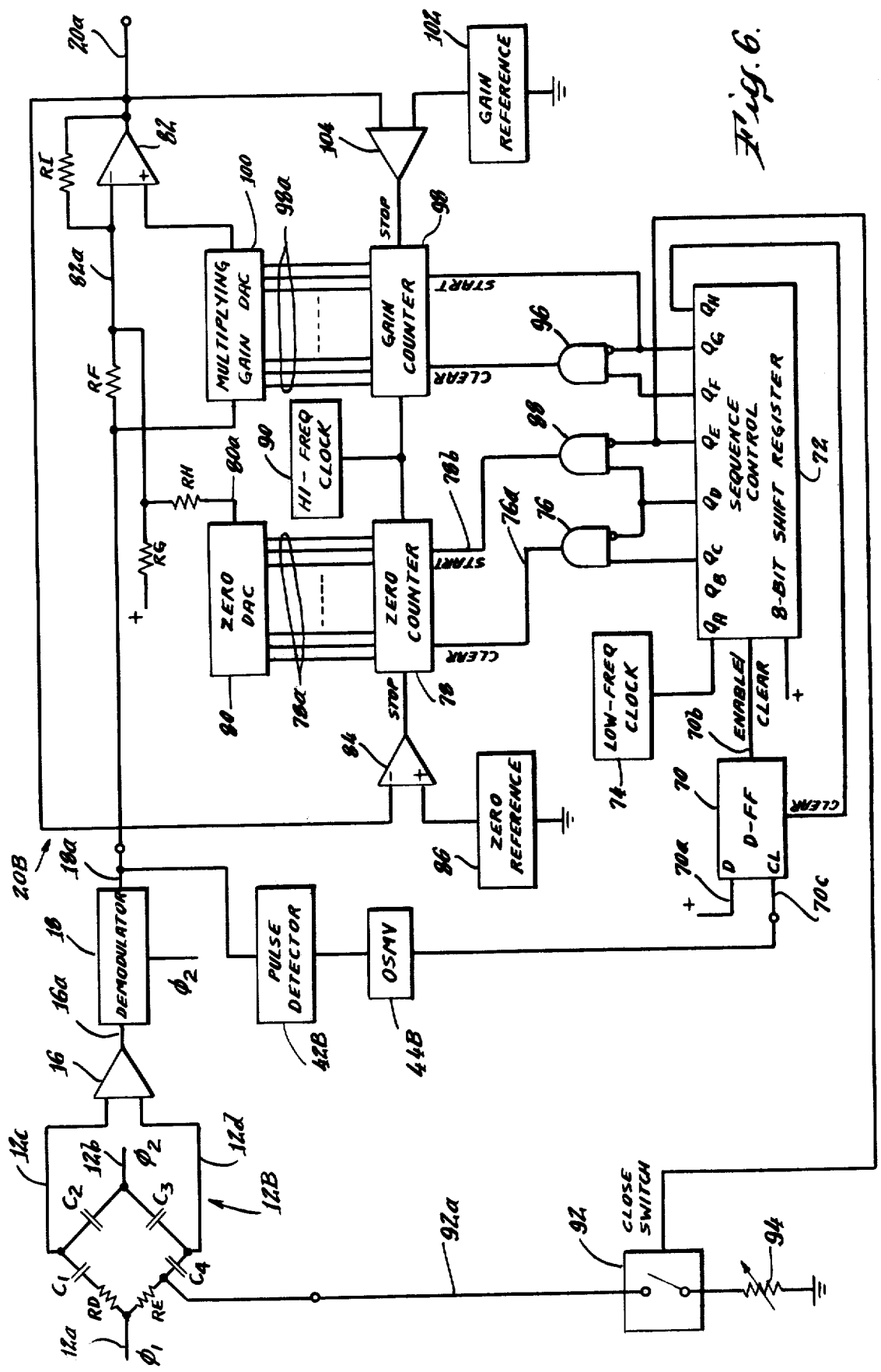
FIG. 6 is a schematic diagram of a circuit for developing both a zero compensating signal and a gain compensating signal for compensating for measurement signal drift in accordance with the present invention.
Figure 7:
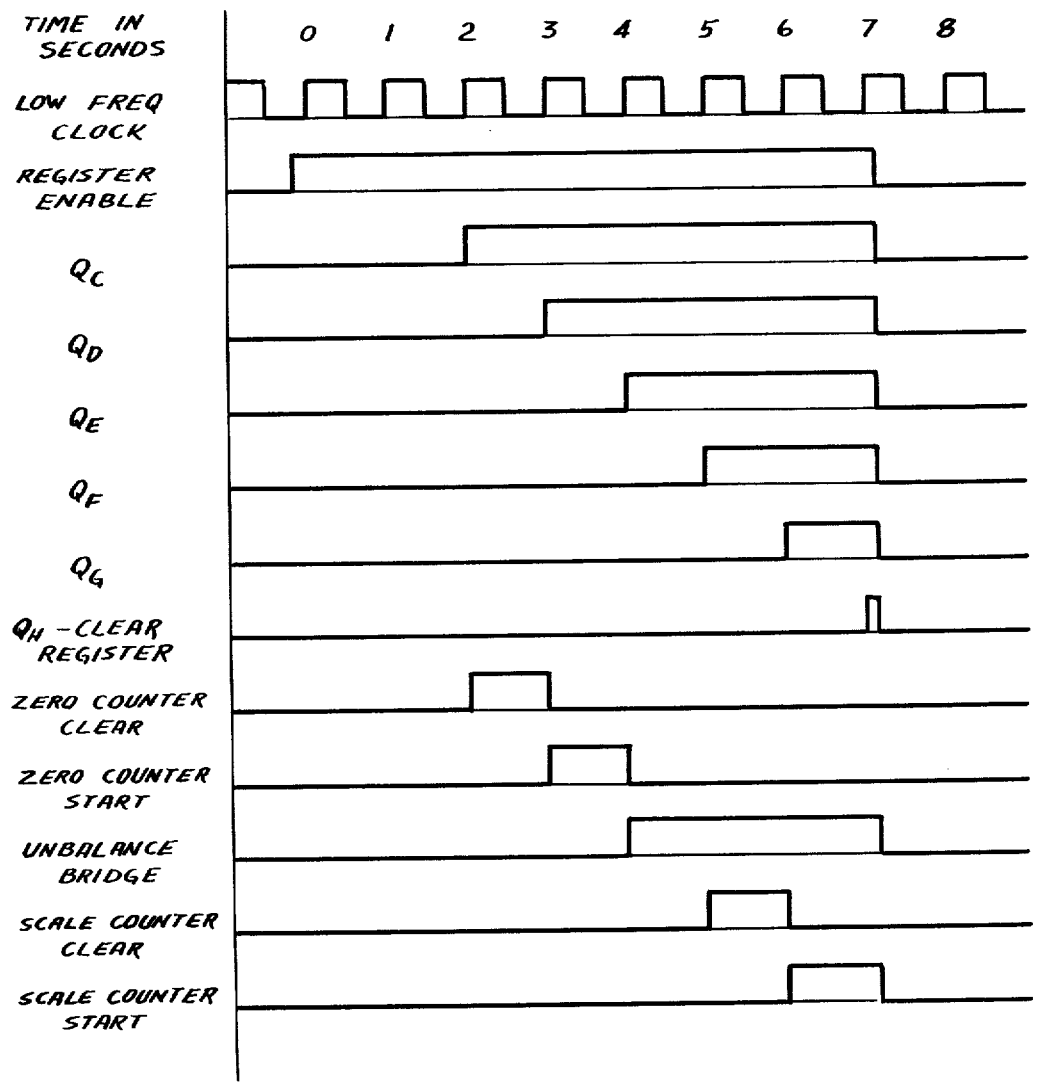
FIG. 7 is a graph of wave forms at selected points in the circuit of FIG. 6.
Figure 8:
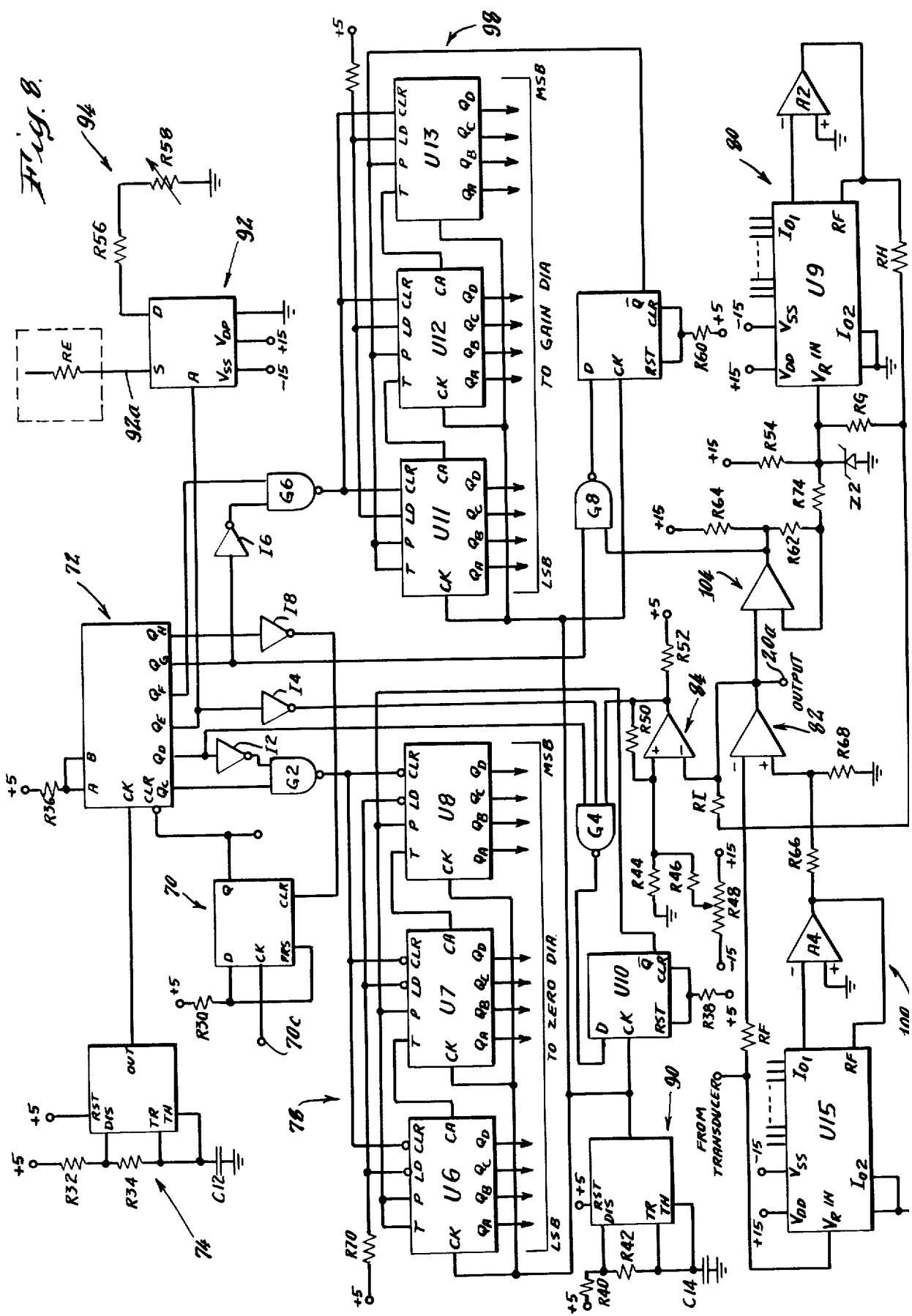
FIG. 8 is a schematic diagram illustrating details of the embodiment of FIG. 6.

The values of the resistors and capacitors in auto-zero circuit 20A in FIG. 5 may take the values indicated below:

R1, R2: 30.9K
R6: 100K
R7: 10K
R8: 56K
R9: 4.7K
R10: 10K
R11: 1M
R15, R16: 22K
R17: 47K
R18: 150
RA: 180K
RB: 80.6K
R22: 1M
R23: 4.99K
R26: 5M
C2: 3.3 microfarads
C6: 4.7 microfarads
C7: 0.1 microfarads
C8: 0.22 microfarads FIGS. 6 through 7 illustrate a preferred embodiment of the auto-calibration circuit 20 in which both auto-zero and auto-gain functions are provided. FIG. 6 is a generalized schematic while FIG. 8 is the more detailed illustration of the circuit. In this embodiment, the capacitive bridge circuit 12b is modified to include identical resistors RD and RE in series with respective capacitors C1 and C4. In normal use of the capacitive sensor, the added resistors have an acceptable constant effect on the gain of the bridge. As before, signals $\phi 1$ and $\phi 2$ are applied to terminals 12a and 12b and the bridge output on lines 12c and 12d are applied to respective inputs to the differential amplifier 16. The amplifier output 16a is applied to the demodulator 18 which also receives the signal $\phi 2$. The demodulator output on line 18a is applied to the auto-calibration circuit 20B.

As in the circuit 20A, removal of the filament from the capacitor sensor is detected by a pulse detector 42B and a one-shot multivibrator 44B. The detected pulse initiates an auto-calibraton sequence which includes an auto-zero sequence followed by an auto-gain sequence. The sequence is controlled by a shift register 72.

The pulse from the one-shot multivibrator 44B is applied as the clock input to a D flip-flop 70 which at all times has a high signal input applied to its D input 70a. Thus, with the flip-flop previously cleared, the output on line 70b goes from low to high with the clock signal from the one-shot multivibrator 44B. The output 70b remains high until a clear signal is received at the end of a sequence.

The high output from the D flip-flop 70 enables a previously cleared eight bit shift register 72. This shift register 72 controls the respective auto-zero and auto-gain sequences to be described. A clock 74 generates a low frequency clock signal which is applied to the clock input of the shift register 72. This low frequency signal may, for example, have a period of about one second. With a one-second clock period, the output QC from the shift register 72 goes high after an approximate two-second delay after removal of the filament from the capacitive sensor bridge. This two-second delay allows the bridge output to stabilize after removal of the filament from the bridge.

A high input is at all times applied to the shift register in order that each output of the register remains high once the initial input has shifted to that stage. Thus, as shown in FIG. 7, the third stage output QC of the register goes high approximately two seconds after the enable signal from the D flip-flop 70. The output remains high until a clear signal is received through the D flip-flop 70 from the final stage output QH. Similarly, the output QD goes high approximately three seconds after the enable signal and remains high until the clear signal is received.

When the QC output goes high and the QD output remains low, a high output is generated by the AND gate 76 and a reset signal 76a is applied to the zero counter 78. At that time the several outputs 78a from the zero counter 78 are reset to zero and the zero digital-to-analog converter 80 has an output 80a of zero.

The demodulated measurement signal, which may be subject to drift from zero even with no filament in the sensor, is applied through resistor RF to the inverting input 82a of the operational amplifier 82. The voltage provided by the voltage drop from the fifteen volt reference supply across resistors RG and RH at the converter 80 output is also connected to the op amp input 82a and is thus summed with the measurement signal. The circuit parameters are selected such that, with the converter 80 output at zero, an approximately one volt positive zero-compensating offset is applied to the op amp 82 by the voltage divider RG, RH. This offset can correct for up to $-1$ volt of zero error from the sensor.

For purposes of further discussion, it will be assumed that the zero error of the sensor is less than the $-1$ volt offset corrected by the zero compensating signal. With such a sensor signal at the op amp input, the output on line 82b is negative. This signal is applied to the inverting input of a comparator 84 which has a zero reference signal from zero reference source 86 applied to its noninverting input. With the negative input to the inverting input of comparator 84, the counter is permitted to enter into a count cycle when a start signal is applied at input 78b.

As illustrated in FIG. 7, the start signal for the zero counter is received approximately one second after the reset signal. When register output QD goes high and output QE remains low, AND gate 88 provides the start signal. The zero counter 78 then begins counting high frequency clock pulses generated by clock oscillator 90. The frequency of these clock pulses is sufficiently high that the counter 78 may count through an entire cycle within the one second interval provided by the register 72.

As zero counter 78 counts up from zero, the output 80a from zero converter 80 steps through negative increments to provide an increasingly negative output 80a. As the output 80a becomes more negative, the voltage applied to the operational amplifier 82 from the voltage divider RG, RH decreases in a fashion similar to that for $V_c$ in FIG. 4. At some point in the continued count of counter 78, the analog compensating signal from the voltage divider directly offsets the measurement signal input to the operational amplifier 82 and the output 82b becomes zero. This point of the counter sequence is detected by the comparator 84 which applied a signal to the counter 78 to stop the count. This signal overrides the start signal on line 78b and the counter holds its last count and thus stores a digital zero compensating signal on lines 78a. This digital compensating signal holds the analog compensating signal summed on line 82a constant throughout subsequent utilization of the capacitive sensor until some later calibration sequence is initiated.

In the remaining portion of the calibration sequence, a signal from the register output QE closes an analog switch 92. By closing this switch, a variable resistor 94 is connected to one leg of the bridge 12b to unbalance the bridge. Thus, even though the filament is still removed from the sensor, a predetermined filament characteristic is simulated in the capacitive sensor bridge. The auto-zero sequence having been completed, the demodulator output on line 18a will then be dependent solely on the simulated characteristic and the gain of the circuit from the bridge through the demodulator, this gain being subject to drift.

Once the resistor 94 is switched into the bridge circuit, a one-second interval is provided by the shift register 72 in order for the measurement signal to stabilize. Then, a reset signal is applied to the gain counter 98 through AND gate 96 when output QF goes high and output QG remains low. With this reset signal, the digital gain compensating signal on line 98a goes to zero.

The gain counter output 98a is applied to a multiplier-type digital-to-analog converter 100. This converter provides an analog output on line 100a proportional to the product of the analog input on line 100b and the digital input on lines 98a. The analog input on line 100b is taken from the measurement signal on line 18a and the analog output 100a is applied to the noninverting input of the operational amplifier 82.

Feedback from the operational amplifier output 82b is applied only through resistor RI to the inverting input 82a. With this circuit configuration, and with the digital input to the multiplying converter 100 set at zero, the gain applied to the measurement signal between line 18a and line 20a is determined solely by the resistances RF and RI. These resistors are selected to set a gain of approximately −0.8.

Approximately one second after the counter 98 is reset to zero, a signal is received from register output QG to start the count of high frequency pulses from clock 90. As the digital gain compensating signal on lines 98a increases, the converter 100 multiplies the measurement signal on line 100b by an increasingly negative amount. The circuit elements are selected such that, as the counter 98 continues to count up, the overall gain on the measurement signal between line 18a and line 20a becomes increasingly negative toward, for example, −1.2. The output on line 20a becomes increasingly negative with the increasingly negative gain applied to the signal on line 18a. When this output on line 20a reaches a predetermined level determined by a standardized gain reference 102, a comparator 104 stops the counting of clock pulses by counter 98. The counter output on line 98a is then held in the counter to store the thus determined digital gain compensating signal which is combined with future measurement signals to compensate for gain drift in the capacitive sensor.

Subsequently, about seven seconds after the shift register 72 is enabled, the output on line QH goes high and a clear signal is applied to D flip-flop 70. The signal on line 70b then clears the shift register and the register remains cleared until some later calibration sequence is initiated through the pulse detector 42B, the one-shot multivibrator 44B, and the D flip-flop 70. With the register cleared the zero counter 78 and gain counter 98 retain their digital compensating signal outputs and the switch 92 is returned to its open position so that the capacitive sensor bridge 12b is returned to its balanced condition.

Although a pulse detector and one-shot multivibrator are shown as the means for initiating the auto-calibration sequence, this need not be the case. For example, the filament may be removed from the capacitive sensor by a solenoid which responds to a control signal from a central control processor, and the D flip-flop 70 might respond to that same control signal. The register output QH could then also provide an end sequence signal to the control processor which would then disable the solenoid and return the filament to its position within the capacitive bridge.

A more detailed circuit for implementing the embodiment of FIG. 6 is shown in FIG. 8. In this circuit, a high signal is applied to the D input of flip-flop 70 through resistor R30. When a signal is received at the clock input on line 70c the Q output of the flip-flop 70 goes high thus removing the clear signal at the inverted clear input of the register. With the clear signal removed, the high input at terminals A and B of the shift register is clocked through the register by the low frequency clock 74. After approximately two seconds, both inputs to the NAND gate G2 (AND gate 76) are high and the inverted clear inputs to the counter 78 go low. Thus the zero counter 78, including three four bit counters U6, U7 and U8, is cleared to a zero output. The several counter outputs leads are connected to the inputs of a multiplying digital-to-analog converter U9.

After approximately three seconds, the QD output of the register and the inverted QE output are applied to a NAND gate G4. The NAND gate G4 has a third input from the zero comparator 84 so that its output serves as both the counter start signal and the counter stop signal. At this point, the third input to the NAND gate G4 is high and with the first two inputs from the register 72 going high the output goes low. This low output is clocked through a D flip-flop U10 to provide a high output at the Q flip-flop output. With the $\overline{Q}$ output of the flip-flop U10 high, each counter U6, U7 and U8 is enabled through its P input and the first counter U6 is triggered at its T input to initiate a count signal. The clock 78 thus begins to increment with clock signals applied from the high frequency clock 90.

With the counter 78 incrementing and its output applied to digital-to-analog converter U9, the analog output from the converter U9 also increments and this positive signal is applied to the inverting input of amplifier A2. The output of the amplifier A2, which is fed back through a feedback resistor in the converter U9, is a negatively incrementing signal applied to one end of the voltage divider circuit RG, RH. The opposite end of the voltage divider is connected to zener diode circuit including diode Z2 which provides a constant positive voltage reference. The output of the voltage divider is summed with the measurement signal at the input to the operational amplifier 82 is compared with a zero reference in comparator 84, the output of which control the NAND gate G4 to provide a stop count signal through flip-flop U10. This signal is applied to the P inputs of the zero counter 78. Due to the difference in clock rates, this stop count signal is received by the counter 78 sometimes before the QE output of control resister 72 goes high.

When the output QE of control register 72 does go high, the counter 78 retains its digital zero compensating signal output and the analog switch 92 is closed to connect registers R56 and R58 into the capacitive bridge circuit through lead 92a. Subsequently, the QF register output goes high. This output is applied along with the inverted QG output through a NAND gate G6 and causes the inverted clear input of each of the four bit counters U11, U12 and U13 of the gain counter 98 to go low. This clears the digital gain compensating signal on the output leads of the counter 98 to go to zero. These output leads are connected to the inputs of multiplying digital-to-analog converter U15 of the gain converter 100.

When output QG of the control shift register finally goes high, it causes the output of NAND gate G8 to go low, thereby providing a high $\overline{Q}$ output from D flip-flop U14. The high output from the D flip-flop enables each stage of the gain counter 98 and initiates a count sequence through input T of counter U11.

The incrementing output from counter 98 is multiplied with the analog measurement signal in the multiplying digital-to-analog converter U15 and provides an incrementing output. This output is applied to the inverting input of an amplifier A4, the output of which is applied across voltage dividing resistors R66 and R68. The divided voltage, which is the product of the measurement signal and some predetermined constant is applied to the noninverting input of the operational amplifier 82. As the output of the gain counter 98 increments, the negative gain applied to the negative measurement signal on line 18a increases. Finally, the positive output on line 20a matches the positive signal applied to the non-inverting input of comparator 104 from zener diode Z2. The output of comparator 104 then goes low causing the D input of flip-flop U14 to go high and the count enabling signal from the flip-flop U14 to the counter 98 to go low thereby terminating the count. At this point, the gain applied to the measurement signal on line 18a due to the digital gain compensating signal at the output of counter 98 is such that the known bridge unbalance results in a standardized output on line 20a.

In FIG. 8, the multiplying digital-to-analog converters U9 and U15 are Analog Devices, Inc. model AD7521 components. The values of the resistors and capacitors in auto-calibration circuit 20b in FIG. 8 may take the values indicated below:

R30: 1K
R32, R34: 470K
R36, R38: 1K
R40, R42: 4.7K
R44: 1K
R46: 1M
R48: 10K, Trim Pot
R50: 1M
R52: 1K
R54: 1K
R56: 4.99K
R58: 10K, Trim Pot
R60: 1K
R62: 1M
R64: 1K
R66: 8.06K
R68: 3.01K
R70, R72, R74: 1K
RF: 10K
RG: 60.4K
RH: 30.1K
RI: 8.06K
C12: 1 μF
C14: 0.01 μF The resistors RD and RE in the bridge circuit are each 499 ohms.

From the foregoing it is apparent that a capacitive measuring and monitoring system may be provided in accordance with the present invention with means to counteract measurement signal drift arising from contamination of the capacitive sensor, using standard components and devices in a circuit that can be constructed easily and at a cost which compares quite favorably with the cost of removing contaminants by frequent cleansing of a sensor head.

While particular preferred examples of auto-calibration circuits accomplishing these goals has been described with reference to FIGS. 5 and 8, it will be understood that other circuit configurations, components, and element values and models can be designed by those skilled in the art to realize the present invention.

Accordingly, although specific embodiments of the invention have been disclosed herein in detail, it is to be understood that this is for the purpose of illustrating the invention, and should not be construed as necessarily limiting the scope of the invention, since it is apparent that many changes can be made to the disclosed structures by those skilled in the art that suit particular applications.

I claim:

1. In a device for continuously monitoring the characteristics of a moving filament by passing the filament through a capacitive sensor and developing an electrical analog signal the magnitude of which represents an absolute measurement of the filament with reference to a prescribed datum or zero point, the improvement which comprises:

means for developing an analog compensating signal to be combined with the analog filament measurement signal to produce a composite signal compensated for measurement signal drift arising from variations in the capacitive sensor, said compensating signal developing means comprising digital signal register means, a digital-to-analog converter having its input coupled to said digital signal register so that said converter produces an analog signal corresponding to the digital signal in said register to serve as said analog compensating signal; and means for controlling the digital signal register to produce an analog compensating signal of value to effect zero condition for said device, the storage of said digital signal in said register eliminating drift in the analog compensating signal.

2. A monitoring device as claimed in claim 1 wherein the means for developing the compensating signal receives a measurement signal from the capacitive sensor absent the filament and comprises:

means for producing a clock pulse train;

means for digitally counting the clock pulses and generating a digital output representative thereof;

digital-to-analog conversion means for developing an analog output signal varying with the digital count;

means for detecting a prescribed comparison between the analog signal and the input measurement signal absent the filament; and means for stopping the clock pulse count when the prescribed comparison is detected;

whereby the analog output signal becomes fixed at a level related to the amount of accumulated signal drift in the capacitive sensor, and the analog output signal may be used to form a compensating signal to be combined with the filament measurement signal to provide accurate absolute measurements.

3. A monitoring device as claimed in claim 2 wherein the means for detecting a prescribed comparison comprises means for adding the analog signal and the measurement signal and means for comparing the added signals with a datum signal.

4. A monitoring device as claimed in claim 2 wherein the analog output signal forms the compensating signal, the compensating signal is combined with the filament measurement signal in an adder, and the means for detecting a prescribed comparison between the analog signal and the input measurement signal comprise means for comparing the output of the adder with a datum signal.

5. A monitoring device as claimed in claim 4 further comprising means for adjusting the datum signal.

6. A monitoring device as claimed in claim 2 wherein the compensating signal developing means is connected to the capacitive sensor to continuously receive the measurement signal therefrom and further comprises pulse detecting means for detecting variations in the measurement signal corresponding to removal of the filament from the capacitive sensor, and wherein the means for producing a clock pulse train and the means for digitally counting the clock pulses are arranged to begin operating when the pulse detector means detects removal of a filament from the capacitive sensor, whereby each time the filament is removed, a new compensating signal will be developed automatically.

7. A monitoring device as claimed in claim 6 wherein the compensating signal developing means further comprises means for generating a gate pulse whenever the pulse detector detects removal of the filament, the means for producing a clock pulse train being responsive to the gate pulse, and the means for digitally counting the clock pulses being reset by the gate pulse.

8. A monitoring device as claimed in claim 1 wherein the compensating signal is combined with the filament measurement signal in an adder, and wherein the means for developing the compensating signal comprises:

pulse detector means for detecting variations in the filament measurement signal corresponding to removal of the filament from the sensor:

means started in response to the pulse detector means for digitally counting clock pulses and for generating a digital output representative thereof;

digital-to-analog conversion means for developing an analog output signal varying with the digital count, said analog output signal forming the compensating signal applied to the adder to be combined with the filament measurement signal;

means for comparing the output of the adder with a datum signal; and means for stopping the counting of clock pulses when the adder output matches the datum signal;

whereby the compensating signal becomes fixed at a level equal to the amount of accumulated signal drift in the capacitive sensor, and the filament measurement signal will be offset by the compensating signal to provide accurate absolute measurements.

9. In a method for continuously monitoring the characteristics of a moving filament by passing the filament through a capacitive sensor and developing an electrical analog signal the magnitude of which represents an absolute measurement of the filament with reference to a prescribed datum or zero point, the improvement which comprises:

developing an analog compensating signal to be combined with the analog filament measurement signal to produce a composite signal compensated for measurement signal drift arising from variations in the capacitive sensor, said compensating signal being developed by (1) forming a digital signal representing a zero-correction to be made to said analog measurement signal to avoid zero offsets, (2) storing said digital signal in its digital format, (3) converting said stored digital signal to a corresponding analog compensation signal, and (4) combining said analog compensating signal to said analog measurement signal, whereby drift in the compensating signal itself is reduced.

10. A monitoring method as claimed in claim 9 wherein the compensating signal is developed by:

producing a clock pulse train;

digitally counting the clock pulses and generating a digital output representative thereof;

converting the digital output into an analog output signal varying with the digital count;

detecting a prescribed comparison between the analog signal and the input measurement signal absent the filament; and stopping the clock pulse count when the prescribed comparison is detected;

whereby the analog signals become fixed at a level related to the amount of accumulated signal drift in the capacitive sensor, and the analog output signal may be used to form a compensating signal to be combined with the filament measurement signal to provide accurate absolute measurements.

11. A monitoring method as claimed in claim 10 wherein the compensating signal and the filament measurement signal are combined by adding the signals together, and wherein the step of detecting a prescribed comparison comprises comparing the added signals with a datum signal.

12. A monitoring method as claimed in claim 10 further comprising detecting pulses in the filament measurement signal corresponding to removal of the filament from the capacitive sensor, and, in response to the detection of each such pulse, starting to generate a digital clock pulse count, whereby each time the filament is removed from the sensor, a new compensating signal will be developed.

13. In apparatus for continuously monitoring a characteristic of a moving elongate filament wherein the filament is passed through a capacitive sensor having means to produce a sensor signal responsive to changes in the capacitance of said sensor, and wherein the zero datum level of said sensor signal may vary with time so as to tend to introduce errors into the accuracy of the measurement; the improvement which comprises:

(A) compensating means for developing a zero-compensating signal and for combining it with said sensor signal so as to produce a composite measurement signal; and (B) zeroizing-control means normally inoperative while said monitoring apparatus is functioning but controllably activatable to establish the zero level of said composite measurement signal at said zero-datum level; said zeroizing-control means including:

(1) a signal-setting circuit to set the value of said zero-compensating signal to a predetermined level which, when said filament is temporarily removed from said sensor, results in a composite measurement signal substantially offset from said zero-datum level;

(2) a signal-varying circuit operable to vary said zero-compensating signal through a range of values from said predetermined level and moving in a direction which alters said composite measurement signal towards said zero-datum level;

(3) a comparator device responsive to said composite measurement signal and operable to produce an output signal indicating when said composite measurement signal has reached said zero-datum level;

(4) means responsive to said comparator signal for stopping the variation of said zero-compensating signal at the particular value which resulted in a signal at said zero-datum level; and (5) a memory device for maintaining said zero-compensating signal at said particular value after said zeroizing-control means has been deactivated and said apparatus has resumed normal operation monitoring the characteristic of said moving filament.

14. Apparatus as claimed in claim 13, wherein said memory device comprises a digital register storing a digital signal representing said zero-compensating signal.

15. Apparatus as claimed in claim 14, wherein said digital register is a counter device; said signal-varying circuit comprising a pulse generator coupled to said counter.

16. Apparatus as claimed in claim 14, wherein said sensor signal is of analog format; and digital-to-analog converter means for converting the digital signal of said register to an analog signal to serve as said zero-compensating signal.

17. In a device for continuously monitoring the characteristics of a moving filament through a capacitive sensor and developing an electrical analog signal to represent an absolute measurement of the filament with reference to a prescribed datum or zero point, the improvement which comprises an automatic zeroizing circuit operable when the filament is removed and including:

a clock pulse oscillator for generating a train of clock pulses;
means for activating said clock pulse oscillator;
a digital counter driven by pulses from said oscillator for generating a digital output signal representing the accumulated count of said clock pulses;
a digital-to-analog converter coupled to said counter for providing a compensating analog output signal which varies with said digital output signal of said digital counter;
a zero reference circuit defining the zero point to which the output of said automatic zeroizing circuit is to be referred;
an adder for adding the analog signal from the capacitive sensor to said compensating analog signal; and
a comparator for comparing the output of said adder to the said zero point of said zero reference circuit and generating a signal to stop the oscillator from generating any further clock pulses when the output values are equivalent;
whereby when said oscillator stops, said counter maintains its digital count and said compensating analog signal continues to be applied to said adder at a value at which it compensates for drift signal in the capacitive sensor when the filament is removed.

18. In a device for continuously monitoring the characteristics of a moving filament by passing the filament through a capacitive sensor and developing an electric filament measurement signal to represent an absolute measurement of the filament with reference to a prescribed datum or zero point, the improvement which comprises:

means for removing said filament from said capacitive sensor;
means for developing a digital compensating signal reflecting the output of said capacitive sensor when said filament is removed from said capacitive sensor and for storing said digital compensating signal in a digital signal storage device; and
means for combining said filament measurement signal with said digital compensating signal to produce a composite signal compensated for measurement signal drift arising from variations in the capacitive sensor, the storage of said digital zero compensating signal in said digital signal storage device eliminating drift in said zero compensating signal.

19. In a method for continuously monitoring the characteristics of a moving filament by passing the filament through a capacitive sensor and developing an electrical filament measurement signal to represent an absolute measurement of the filament with reference to a prescribed datum or zero point, the improvement which comprises:

removing said filament from said capacitive sensor;
while said filament is removed, developing a digital compensating signal reflecting the output of said capacitive sensor and storing said digital compensating signal in a digital signal storage device;
returning said filament to said capacitive sensor; and
combining said filament measurement signal with said digital compensating signal to produce a composite signal compensated for measurement signal drift arising from variations in the capacitive sensor, the storage of said digital compensating signal in said digital signal storage device eliminating drift in said compensating signal.

20. In a device for continuously monitoring the characteristics of a moving filament by passing the filament through a capacitive sensor and developing an electric filament measurement signal to represent an absolute measurement of the filament with reference to a prescribed datum or zero point, the improvement which comprises:

means for simulating in said capacitive sensor a predetermined filament characteristic;
means for developing and storing in a digital signal storage device a digital gain compensating signal reflecting the necessary gain to be applied to said measurement signal to provide a predetermined signal; and
means for combining said filament measurement signal with said digitally stored gain compensating signal to produce a signal compensated for gain drift arising from variations in the capacitive sensor, the storage of said digital gain compensating signal in said digital signal storage device eliminating drift in said gain compensating signal.

21. A monitoring device as claimed in claim 20 wherein the means for developing and storing said digital gain compensating signal receives a measurement signal from the capacitive sensor and comprises:

means for producing a clock pulse train;
means for digitally counting the clock pulses and generating a digital output representative thereof;
means including a digital-to-analog converter for adjusting the gain of said measurement signal with the digital count;
means for detecting a prescribed comparison between the adjusted-gain measurement signal and a standardized signal; and
means for stopping the clock pulse count when the prescribed comparison is detected;
whereby the digital gain compensating signal becomes fixed at a level related to the amount of accumulated gain drift in the capacitive sensor and may be combined with the filament measurement signal to provide accurate absolute measurement.

22. A monitoring device as claimed in claim 21 wherein:

said means for adjusting the gain of the measurement signal includes an operational amplifier having a feedback resistor connected between an output and one input,
said measurement signal is applied through an input resistor to said one input of said operational amplifier; and
said digital-to-analog converter is a multiplying type and said measurement signal is applied through said multiplying digital-to-analog converter to the other input of said operational amplifier.

23. A monitoring device as claimed in claim 21 wherein the compensating signal developing means is connected to the capacitive sensor to continuously receive the measurement signal therefrom and further comprises pulse detecting means for detecting variations in the measurement signal corresponding to removal of the filament from the capacitive sensor, and wherein the means for producing a clock pulse train and the means for digitally counting the clock pulse are arranged to begin operating when the pulse detector means detects removal of a filament from the capacitive sensor, whereby each time the filament is removed, a new compensating signal will be developed automatically.

24. A monitoring device as claimed in claim 21 wherein said means for simulating a predetermined filament characteristic in said capacitive sensor comprises balancing circuit elements in opposed legs of said capacitive bridge and means for connecting an additional circuit element into only one of said legs to unbalance said capacitive bridge.

25. In apparatus for continuously monitoring a characteristic of a moving elongate filament wherein the filament is passed through a capacitive sensor having means to produce a sensor signal responsive to changes in the capacitance of said sensor, and wherein the gain of said sensor signal may vary with time so as to tend to introduce errors into the accuracy of the measurement; the improvement which comprises:
(A) compensating means for developing a gain-compensating signal and for combining it with said sensor signal so as to produce a composite measurement signal; and
(B) control means normally inoperative while said monitoring apparatus is functioning but controllably activatable to establish the gain of said composite measurement signal at a predetermined level; said control means including;
(1) a signal-setting circuit to set the value of said gain-compensating signal to an offset level which, when said filament is temporarily removed from said sensor and a predetermined characteristic is simulated, results in a composite measurement signal substantially offset from said predetermined level;
(2) a signal-varying circuit operable to vary said gain-compensating signal through a range of values from said offset level and moving in a direction which alters said composite measurement signal towards said predetermined level;
(3) a comparator device responsive to said composite measurement signal and operable to produce an output signal indicating when said composite measurement signal has reached said predetermined level;
(4) means responsive to said comparator signal for stopping the variation of said gain-compensating signal at the particular value which resulted in a signal at said predetermined level; and
(5) a memory device for maintaining said gain-compensating signal at said particular value after said control means has been deactivated and said apparatus has resumed normal operation monitoring the characteristic of said moving filament.

26. In a method for continuously monitoring the characteristics of a moving filament by passing the filament through a capacitive sensor and developing an electric filament measurement signal to represent an absolute measurement of the filament with reference to a prescribed datum or zero point, the improvement which comprises:
simulating in said capacitive sensor a predetermined filament characteristic;
while simulating said filament characteristic, developing and storing in a digital signal storage device a digital gain compensating signal reflecting the necessary gain to be applied to said measurement signal to provide a predetermined signal;
ending said filament characteristic simulation;
combining said filament measurement signal with said digitally stored gain compensating signal to produce a signal compensated for gain drift arising from variations in the capacitive sensor the storage of said digital gain compensating signal in said digital signal storage device eliminating drift in said gain compensating signal.

27. A monitoring method as claimed in claim 26 wherein said filament characteristic is simulated in said capacitive sensor by switching a circuit element into a leg of said capacitive bridge.

28. In a device for continuously monitoring the characteristics of a moving filament by passing the filament through a capacitive sensor and developing an electric filament measurement signal to represent an absolute measurement of the filament with reference to a prescribed datum or zero point, the improvement which comprises:
means for controlling respective auto-zero and auto-gain sequences when said filament is removed from said capacitive sensor;
means for developing during said auto-zero sequence a digital zero compensating signal reflecting the output of said capacitive sensor when said filament is removed and for storing said digital zero compensating signal in a digital signal storage device;
means for simulating in said capacitive sensor during said auto-gain sequence a predetermined filament characteristic;
means for developing and storing in a digital signal storage device a digital gain compensating signal reflecting the necessary gain to be applied to said measurement signal to provide a predetermined signal; and
means for combining said filament measurement signal with said digitally stored zero compensating signal and said digitally stored gain compensating signal to produce a signal compensated for both zero drift and gain drift arising from variations in the capacitive sensor, the digital storage of said compensating signals eliminating drift in said compensating signals.

29. In a method for continuously monitoring the characteristics of a moving filament by passing the filament through a capacitive sensor and developing an electric filament measurement signal to represent an absolute measurement of the filament with reference to a prescribed datum or zero point, the improvement which comprises:
removing said filament from said capacitive sensor;
while said filament is removed, developing a digital zero compensating signal reflecting the output of said capacitive sensor and storing said digital zero compensating signal in a digital signal storage device;
simulating in said capacitive sensor a predetermined filament characteristic;

developing and storing in a digital signal storage device a digital gain compensating signal reflecting the necessary gain to be applied to said measurement signal to provide a predetermined signal;

removing said filament characteristic simulation and returning said filament to said capacitive sensor; and combining said filament measurement signal with said digitally stored zero compensating signal and said digitally stored gain compensating signal to produce a signal compensated for both zero drift and gain drift arising from variations in the capacitive sensor, the digital storage of said compensating signals eliminating drift in said compensating signals.

30. In a device for continuously monitoring the characteristics of a moving filament by passing the filament through a capacitive sensor and developing an electric filament measurement signal to represent an absolute measurement of the filament with reference to a prescribed datum or zero point, the improvement which comprises:

means for simulating in said capacitive sensor a predetermined filament characteristic;

means responsive to said sensor when subject to said simulating means and operable to develop and store in a memory device a gain compensating signal reflecting the necessary gain to be applied to said measurement signal to provide a predetermined signal;

means for controlling said filament measurement signal in accordance with said stored gain compensating signal to produce a signal compensated for gain drift arising from variations in the capacitive sensor, the storage of said gain compensating signal in said memory device eliminating drift in said gain compensating signal.

31. In a method for continuously monitoring the characteristics of a moving filament by passing the filament through a capacitive sensor and developing an electric filament measurement signal to represent an absolute measurement of the filament with reference to a prescribed datum or zero point, the improvement which comprises:

simulating in said capacitive sensor a predetermined filament characteristic;

while simulating said filament characteristic developing and storing in a memory device a gain compensating signal reflecting the necessary gain to be applied to said measurement signal to provide a predetermined signal;

ending said filament characteristic simulation; and controlling said filament measurement signal in accordance with said stored gain compensating signal to produce a signal compensated for gain drift arising from variations in the capacitive sensor, the storage of said gain compensating signal in said memory device eliminating drift in said gain compensating signal.

* * * * *